US012636027B2

(12) United States Patent
    Jones

(10) Patent No.: US 12,636,027 B2
(45) Date of Patent: May 26, 2026

(54) GUIDEWIRE LOADING SYSTEMS

(71) Applicant: Bard Peripheral Vascular, Inc.,
    Franklin Lakes, NJ (US)

(72) Inventor: Austin T. Jones, Tempe, AZ (US)

(73) Assignee: Bard Peripheral Vascular, Inc.,
    Franklin Lakes, NJ (US)

( * ) Notice: Subject to any disclaimer, the term of this
    patent is extended or adjusted under 35
    U.S.C. 154(b) by 712 days.

(21) Appl. No.: 17/970,937

(22) Filed: Oct. 21, 2022

(65)             Prior Publication Data

US 2024/0130748 A1      Apr. 25, 2024
    US 2024/0225672 A9      Jul. 11, 2024

(51) Int. Cl.
    *A61B 17/221*        (2006.01)
    *A61B 17/22*         (2006.01)

(52) U.S. Cl.
    CPC .. *A61B 17/221* (2013.01); *A61B 2017/22038*
                                    (2013.01)

(58) Field of Classification Search
    CPC ........ A61B 17/221; A61B 2017/22038; A61B
                2017/00358; A61B 17/3468; A61B
                2017/7347; A61M 25/09041; A61M
                2/011; A61M 2/954; A61M 2002/5928;
                                    A61M 2002/5934
    See application file for complete search history.

(56)             References Cited

U.S. PATENT DOCUMENTS 4,509,944 A * 4/1985 King ................ A61M 25/0014
                                                604/528
    5,683,411 A * 11/1997 Kavteladze ...... A61B 17/12172
                                                606/200

5,971,991 A * 10/1999 Sunderland ........ A61M 25/0113
                                                606/108
    6,110,146 A * 8/2000 Berthiaume .... A61M 25/09041
                                                604/103.05
    9,655,635 B2 5/2017 Gehle
    9,717,888 B2 * 8/2017 Sos ..................... A61M 25/002
    9,757,542 B2 9/2017 Lupton
    10,548,706 B2 2/2020 Laroya et al.
    10,729,454 B2 8/2020 Root et al.
    2004/0181237 A1 * 9/2004 Forde .............. A61B 17/12122
                                                623/1.11

(Continued)

FOREIGN PATENT DOCUMENTS

WO        2000020064 A1     4/2000

OTHER PUBLICATIONS

Merit Medical, EN Snare® Endovascular Snare System, https://
www.merit.com/peripheral-intervention/intervention/snares-accessories/
en-snare-endovascular-snare-system/, Jul. 16, 2021.

*Primary Examiner* — Kathleen S Holwerda
*Assistant Examiner* — James R McGinnity
(74) *Attorney, Agent, or Firm* — Dinsmore & Shohl LLP

(57)             ABSTRACT

A guidewire loading system includes a catheter having a
catheter body having an internal lumen and a snare. The
snare is positioned at least partially within the internal lumen
of the catheter body. The snare includes a snare body and a
first capture flare extending from a first end of the snare body
and configured to receive the guidewire. The catheter body
compresses the first capture flare to form a friction grip
around the guidewire when the snare, including the first
capture flare, and guidewire are pulled at least partially
through the internal lumen of the catheter body.

13 Claims, 5 Drawing Sheets

(56)                    References Cited

U.S. PATENT DOCUMENTS

| | | | |
|---|---|---|---|
| 2005/0159770 A1* | 7/2005 | Divani | .................. A61M 29/00 |
| | | | 606/200 |
| 2008/0114390 A1* | 5/2008 | Guinan | ........... A61M 25/09041 |
| | | | 606/194 |
| 2014/0025086 A1 | 1/2014 | Rottenberg et al. | |
| 2017/0119410 A1 | 5/2017 | MacTaggart et al. | |
| 2023/0225717 A1* | 7/2023 | Neustadter | ....... A61B 17/00234 |
| | | | 606/113 |

* cited by examiner

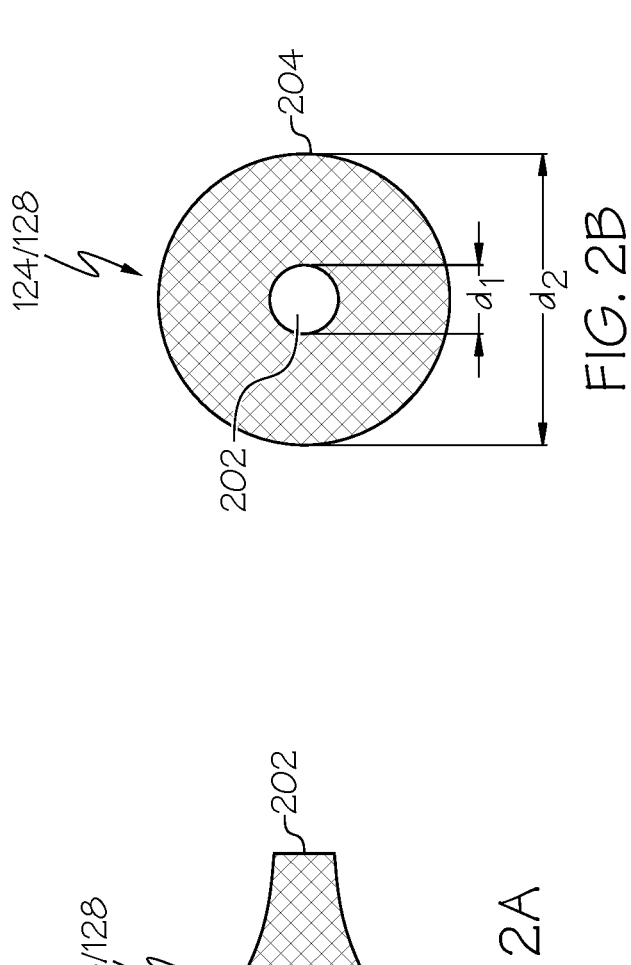
FIG. 2B
FIG. 2A
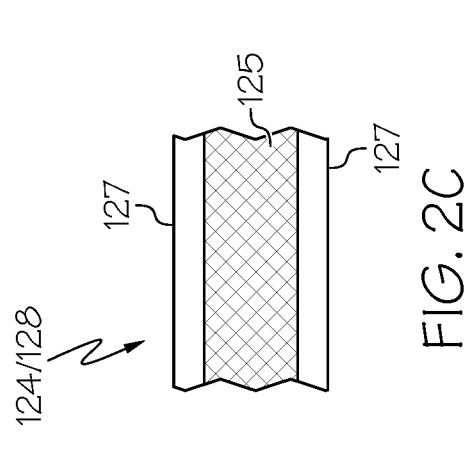
FIG. 2C

GUIDEWIRE LOADING SYSTEMS

TECHNICAL FIELD

The present disclosure relates to assemblies, systems, and methods for loading guidewires into catheters.

BACKGROUND

Guidewires are commonly used to deliver one or more instruments over in the vasculature of a subject. For example, guidewires serve to provide a trackable guide over or along which a catheter may be advanced. Prior to insertion of the guidewire and/or catheter into the subject's vasculature, the catheter is loaded over the guidewire. That is, the guidewire is fed through the catheter and maneuvered through the subject's vasculature. The catheter is then advanced or tracked over the guidewire to a desirable location in the subject's anatomy. As the guidewires and catheters are sized to traverse through the subject's vasculature, and the guidewires are particularly sized to pass through the catheters, the small diameters of the guidewires and catheters may result in an operator needing to exercise a high degree of precision to load the guidewire into the catheter. It may be useful to have guidewire loading systems that reduce the precision necessary to load guidewires into catheters.

SUMMARY

In one embodiment, a guidewire loading system includes a catheter comprising a catheter body defining an internal lumen and a snare at least partially positioned within the internal lumen of the catheter body. The snare includes a snare body and a first capture flare extending from a first end of the snare body and configured to receive a guidewire. The catheter body compresses the first capture flare to form a friction grip around the guidewire when the snare, including the first capture flare, and the guidewire are pulled at least partially through the internal lumen of the catheter body.

In another embodiment, a guidewire snare includes a snare body, a first capture flare extending from a first end of the snare body and configured to receive a guidewire, and a second capture flare extending from a second end of the snare body and configured to receive the guidewire. The first capture flare is configured to form a friction fit around the guidewire when the first capture flare is pulled at least partially through an internal lumen of a catheter body. The second capture flare is configured to form a friction fit around the guidewire when the second capture flare is pulled at least partially through the internal lumen of the catheter body.

In yet another embodiment, a method of loading a guidewire into a catheter includes advancing the guidewire into a capture flare of a snare. The snare includes a snare body, and the capture flare extending from an end of the snare body and configured to receive the guidewire. The snare body is positioned at least partially within an internal lumen of a catheter body of the catheter. The capture flare at least partially extends outside the internal lumen of the catheter body. The method further includes pulling the snare and the guidewire at least partially through the internal lumen of the catheter body such that the catheter body compresses the capture flare to form a friction grip around the guidewire.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 2A schematically depicts a side view of a first capture flare of the snare of FIG. 1, according to one or more embodiments shown and described herein;

FIG. 2B schematically depicts an axial view of the first capture flare of FIG. 2A, according to one or more embodiments shown and described herein;

FIG. 2C schematically depicts various layers of the first and/or second capture flare of FIG. 2A, according to one or more embodiments shown and described herein;

DETAILED DESCRIPTION

A guidewire may be used to pass one or more treatment devices, including catheters, into the vasculature of a subject. Loading guidewires into catheters prior to placement of either instrument into the vasculature of a subject may be cumbersome for physicians. As both instruments may be sized sufficiently small to traverse through a subject's vasculature, it may require a high degree of precision to thread a guidewire through a catheter, which may have a diameter only slightly larger than that of the guidewire. The embodiments described herein address the one or more aforementioned limitation.

In particular, the devices, system, and methods for loading a guidewire into a catheter described herein include guidewire snares having one or more capture flares. The guidewire snare may come pre-loaded into a catheter such that the snare is already contained within the catheter body when the device/system is delivered to a physician or user. A capture flare extends from an end of a snare body of the snare. An open end of the capture flare has a diameter greater than that of the catheter body, such that a physician may be able to insert the guidewire into the capture flare with a lesser degree of precision than needed to insert the guidewire directly into the catheter body. The guidewire and snare may then be advanced into the catheter body, which is sized to exhibit a compression force on the capture flare, causing the capture flare to collapse and form a friction grip around the guidewire. A second end of the snare may then be manipulated without the need to independently handle the guidewire, to advance the guidewire fully through the catheter body. Various embodiments will now be described in greater detail below with reference to the figures.

As used herein, the term "proximal" means closer to or in the direction of an origin of an element, such as a catheter. The origin of a catheter may be a handle or other user-manipulated portion of the catheter. The term "distal" means further from the origin, or handle, of the catheter. Put another way, the term "distal" means closer to or in the direction of a tip of a catheter, which is separated from a handle of the catheter by the length of the catheter body.

Figure 1:
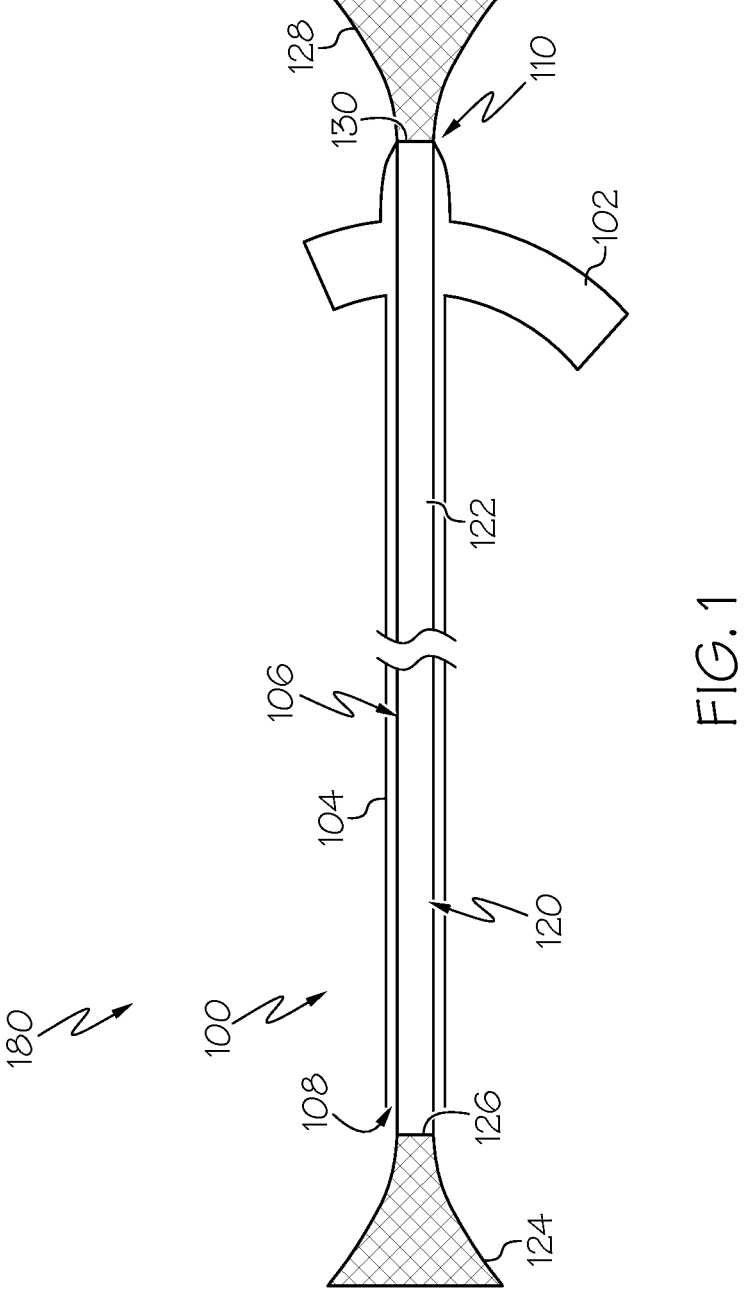
FIG. 1 schematically depicts a guidewire loading system including a catheter and a pre-loaded snare, according to one or more embodiments shown and described herein.

Referring now to FIG. 1, an interior portion a catheter 100 is depicted. The catheter 100 may be sized and shaped for use in any number of treatment procedures, including but not limited to, atherectomy procedures, bypass procedures, fistula formation procedures, and hemodialysis. The catheter 100 may include a handle 102, with which a user can manipulate the catheter 100. The catheter 100 includes a catheter body 104 having an internal lumen 106. The diameter of the internal lumen 106 may be any diameter sufficient to provide clearance to allow a a guidewire to pass. For example in some embodiments, the diameter may be between about 0.1 mm and 1 mm, such as between about 0.2 mm and 0.8 mm, such as about 4 mm to about 5 mm, though other diameters are contemplated and possible. The catheter body 104 defines a distal opening 108 and a proximal opening 110. The distal opening 108 and the proximal opening 110 provide access to the internal lumen 106 of the catheter body 104. The distal opening 108 and the proximal opening 110 allow for passage of one or more instruments through the internal lumen 106 of the catheter body 104. The catheter 100 may be formed of any convention catheter material such latex, silicone, Teflon, rubber, polyurethane, or the like.

A snare 120 is positioned within the internal lumen 106 of the catheter body 104. The snare 120 may be "pre-loaded" within the catheter 100. In other words, a physician or other end user need not insert the snare 120 into the catheter 100. Instead, the catheter 100 and snare 120 may be assembled into a device/system 180 by a manufacturer, for instance, and provided to the end user in its assembled form. The snare 120 includes a snare body 122. The snare 120 includes a first capture flare 124 positioned at and extending from a first end 126 of the snare body 122. The snare 120 may also include a second capture flare 128 positioned at and extending from a second end 130 of the snare body 122.

The snare body 122 may be any size such that the snare body 122 may fit within the catheter body 104. Moreover, as explained in further detail below, the snare body 122 may be sized such that the snare body 122 is moveable within and through the catheter body 104. That is, an outer diameter of the snare body 122 is less than the inner diameter of the catheter body 104. The snare body 122 may be formed of any desirable material, including one or more polymers and/or metals. The snare body 122 may be solid or hollow. Accordingly, the snare body 122 may be a rod, a tube, a wire. The snare body 122 may be flexible or rigid.

As noted above, the snare 120 may be pre-loaded within the catheter 100. When pre-loaded, and prior to user manipulation, the snare 120 may be described as being in a pre-loaded configuration. In the pre-loaded configuration, the first capture flare 124 and/or the second capture flare 128 are positioned to receive a guidewire 300. In the pre-loaded configuration, the first capture flare 124 at least partially extends outside of the internal lumen 106 of the catheter body 104. In embodiments, in the pre-loaded configuration, the entirety of the first capture flare 124 may be positioned outside of the internal lumen 106 of the catheter body 104. In the pre-loaded configuration, the second capture flare 128 may at least partially extends outside of the internal lumen 106 of the catheter body 104. In embodiments, in the pre-loaded configuration, the entirety of the second capture flare 128 may be positioned outside of the internal lumen 106 of the catheter body 104.

Referring to FIG. 1 and FIG. 2A, which depict a side view of the first capture flare 124 when the snare 120 is in the pre-loaded configuration, the first capture flare 124 may flare outwardly from its coupled end 202 to its open end 204. The coupled end 202 of the first capture flare 124 may be the end of the capture flare 124 coupled (e.g., via welding, brazing, adhesion, or the like) to the first end 126 of the snare body 122. As depicted in in FIG. 2B, which depicts an axial view of the first capture flare 124 when the snare 120 is in the pre-loaded configuration, by flaring outward, the first capture flare 124 may have a first diameter, d1, at its coupled end 202 and a second diameter, d2, at its open end 204, where the second diameter, d2, is greater than the first diameter, d1. The second diameter, d2, of the open end 204 of the first capture flare 124 is greater than the outer diameter of the snare body 122. The second diameter, d2, of the open end 204 of the first capture flare 124 is greater than the outer diameter of the catheter body 104 thereby providing a funnel-like guide into the catheter body 104.

When the snare 120 is in the pre-loaded configuration, the second diameter, d2, of the open end 204 is the maximum outer diameter of the first capture flare 124. The first capture flare 124 may be conical or frustoconical in shape. The first capture flare 124 may be made of any material suitable for snaring a guidewire 300. The first capture flare 124 may be made of one or more plastics, polymers, and/or metals. The first capture flare 124 may be formed of a mesh of one or more plastic, polymer, and/or metals. As a mesh, the first capture flare 124 may include a plurality of intertwined wires or rods. In some embodiments such as generally depicted in FIG. 2C, the first capture flare 124 may be made of a polymeric film. In embodiments, the first capture flare 124 may be include both a mesh 125 and polymeric film 127, such that the wire mesh is enveloped between two sheets of polymeric film. Stated another way, the first capture flare 124 may include the mesh 124 with a first polymeric film layer on a first side or major surface of the mesh 124 and a second polymer film layer on a second side or major surface of the mesh 124 opposite the first or major surface. The polymeric film may be formed of any suitable material such as, but not limited to, Pebax, Nylon, polyethylene, polypropylene, and polyurethane. The polymeric film 127 may assist in gripping the guidewire and moving the guidewire relative to the catheter body 104.

While the first capture flare 124 has been discussed in detail, it should be appreciated that the same description may apply to the second capture flare 128. For instance, the second capture flare 128 may flare outwardly from its coupled end to its open end. The coupled end of the second capture flare 128 may be the end of the second capture flare 128 coupled to the second end 130 of the snare body 122, as illustrated in FIG. 1. By flaring outward, the second capture flare 128 may have a first diameter at its coupled end and a second diameter at its open end, where the second diameter is greater than the first diameter. The second diameter of the open end of the second capture flare 128 is greater than the outer diameter of the snare body 122. The second diameter of the open end of the second capture flare 128 is greater than the outer diameter of the catheter body 104. When the snare 120 is in the pre-loaded configuration, the second diameter of the open end 204 is the maximum diameter of the first capture flare 124. The second capture flare 128 may be conical or frustoconical in shape. The second capture flare 128 may be made of any desirable material. The second capture flare 128 may be made of one or more plastics, polymers, and/or metals. The second capture flare 128 may be formed of a mesh of one or more plastic, polymer, and/or metals. As a mesh, the second capture flare 128 may include a plurality of intertwined wires or rods. In embodiments, the second capture flare 128 may be made of a polymeric film. In embodiments, the second capture flare 128 may be include both a mesh and polymeric film, such that the wire mesh is enveloped between two sheets of polymeric film as describe above.

Figure 3:
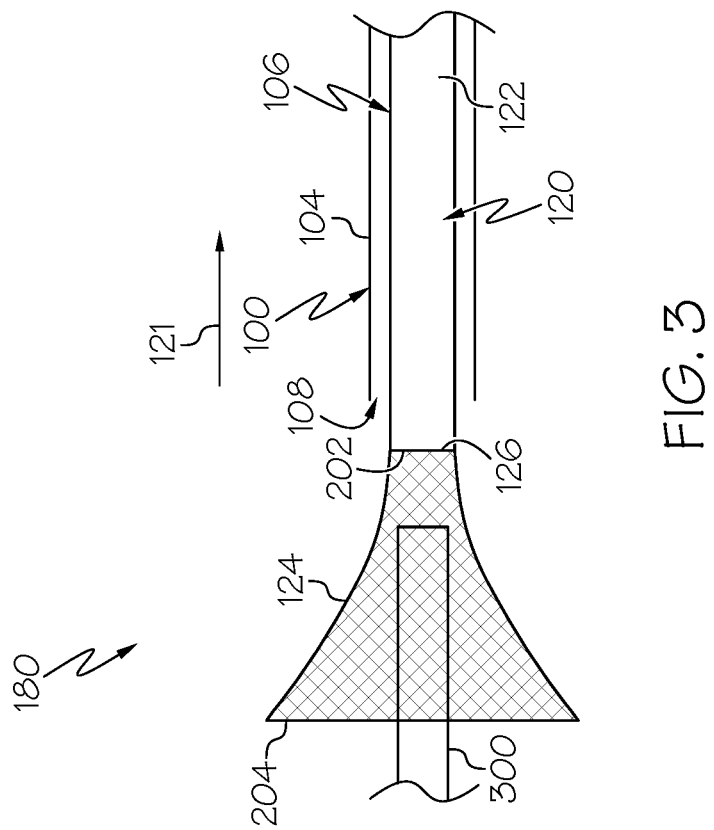
FIG. 3 schematically depicts the guidewire loading system of FIG. 1 having a guidewire positioned within the capture flare of the snare, according to one or more embodiments shown and described herein.

Referring now to FIG. 3, in conjunction with FIGS. 1 and 2A, the distal end 108 of the catheter body 104 of the catheter 100 is depicted with the snare 120 in the pre-loaded configuration. In operation, a user may advance a guidewire 300 into the open end 204 of the first capture flare 124. The second diameter of the open end 204 of the first capture flare 124 is, therefore, larger than the diameter of the guidewire 300. The funneled shape of the first capture flare 124 effectively directs the guidewire 300 toward the snare body 122.

Figure 4:
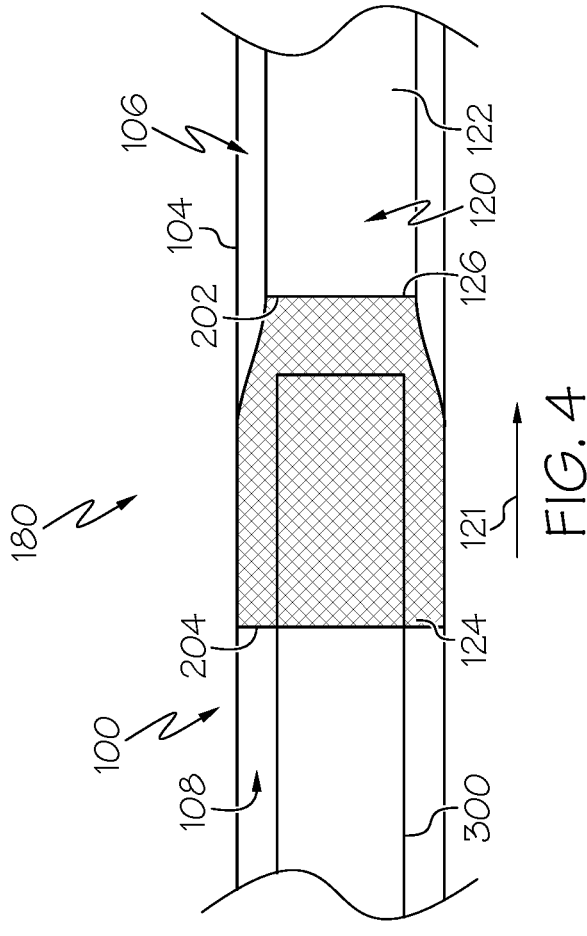
FIG. 4 schematically depicts a cross section the guidewire loading system of FIG. 3 with the capture flare in a compressed configuration, according to one or more embodiments shown and described herein.

Referring now to FIG. 4, in conjunction with FIGS. 1, 2A, and 3, the distal end 108 of the catheter body 104 of the catheter 100 is depicted with the first capture flare 124 in a compressed or collapsed state. To load the guidewire 300 into the catheter 100, a user may push (as shown by arrow 121) or pull the snare 120, with the guidewire 300 within the first capture flare 124 through the internal lumen 106 of the catheter body 104. More particularly, and as depicted in FIG. 4, to load the guidewire 300 into the catheter 100, a user may advance the snare 120 such that the first capture flare 124, including the guidewire 300 within, passes into the internal lumen 106 of the catheter body 104 through the distal opening 108 of the catheter body 104. As the first capture flare 124 enters the distal opening 108 of the catheter body 104, the catheter body 104 compresses the first capture flare 124 such that the first capture flare 124 collapses. That is, the inner wall of the catheter body 104 exhibits a force on the first capture flare 124 causing the first capture flare 124 to compress such that the first capture flare 124 fits within and may be advanced through the internal lumen 106 of the catheter body 104. When the first capture flare 124, is positioned within the internal lumen 106 of the catheter body 104, the first capture flare 124 and the snare 120 may be considered to be in a compressed configuration. In the compressed configuration, the snare 120 has a maximum diameter less than the maximum diameter of the snare in the uncompressed, pre-loaded configuration When the first capture flare 124 compresses or collapses from the force exhibited by the catheter body 104, the first capture flare 124 forms a friction grip around the portion of the guidewire 300 positioned within the first capture flare 124. In embodiments, the thickness and/or maximum diameter of the first capture flare 124 when the snare 120 is in the pre-loaded configuration, may contribute to the friction grip formed around the guidewire 300. More particularly, the capture flare 124 may be sized and shaped such that the material of the first capture flare 124, such as the mesh or film, fills the void within the internal lumen 106 between the inner wall of the catheter body 104 and the outer surface of the guidewire 300 when the first capture flare 124 collapses thereby providing enough force to reliably grip the guidewire.

In some embodiments, the first capture flare 124 and/or the second capture flare 128 may be naturally biased to an open configuration. In other words, the natural resting state of the capture flare 124/128 may be in the open configuration. Referring still to the present embodiment with the first capture flare 124, the force exhibited on the first capture flare 124 by the catheter body 104 as the first capture flare 124, including the guidewire 300, is advanced into the internal lumen 106 of the catheter body 104, encourages the first capture flare 124 to transition from its natural resting state (i.e. the open configuration) to a closed configuration. By moving the first capture flare 124 to the closed configuration the first capture flare 124 seals to grips onto the guidewire 300 positioned within the first capture flare 124.

Due to the friction grip formed around the guidewire 300 by the first capture flare 124, a user may grab the snare 120 from the opposite end (e.g., the proximal end) and pull the snare 120 and guidewire 300 through the catheter body 104 without the need to independently handle or manipulate the guidewire 300. That is, the friction grip formed on the guidewire 300 by the first capture flare 124 may be sufficiently strong such that a tensile force applied to the second capture flare 128, for instance, is transmitted through snare body 122 to the first capture flare 124 and guidewire 300, without the guidewire 300 escaping from the first capture flare 124. In some embodiments, it is contemplated that the snare 120 may instead be held stationary, and the catheter 100 advanced over the snare 120 to move the catheter along the guidewire 300.

Figure 5:
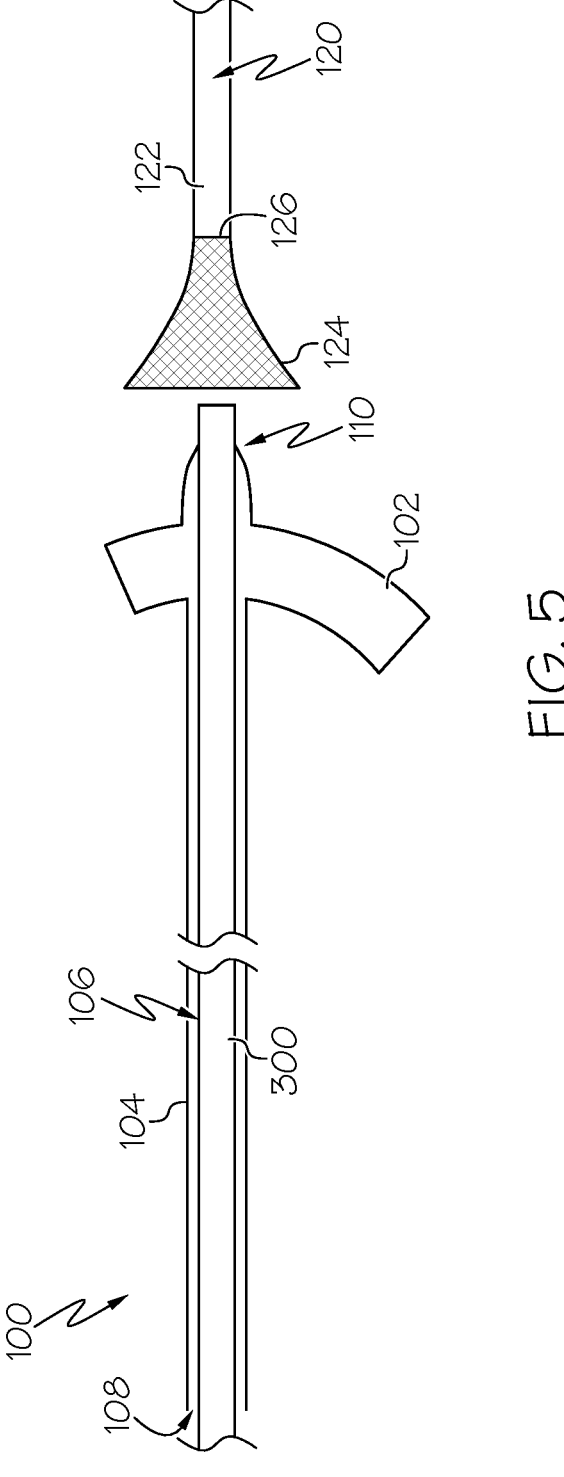
FIG. 5 schematically depicts the catheter of FIG. 1 containing a loaded guidewire, according to one or more embodiments shown and described herein.

As depicted in FIG. 5, and with additional reference to FIGS. 1, 2A, and 4, a user may advance the snare 120, including the captured guidewire 300, (e.g., by pulling the snare 120 from the second end 130 of the snare body 122 or advancing the catheter 100 distally over the snare 120) until the entirety of the snare body 122 and the first capture flare 124 are passed out of the second open end 110 of the catheter body 104. When the first capture flare 124 passes out of the second open end 110 of the catheter body 104, the catheter body 104 no longer exhibits a force on the first capture flare 124. Therefore, without the force of the catheter body 104, the first capture flare 124 may transition back into the pre-loaded configuration, as depicted in FIG. 2A. As the first capture flare 124 returns to the pre-loaded configuration, the first capture flare 124 loosens its friction grip on the guidewire 300, such that the snare 120 and guidewire 300 may be independently manipulated. By passing the first capture flare 124, including the guidewire 300, from an initial pre-loaded position extending outside the first open end 108 of the catheter body 104, through the catheter body 104 and the second open end 110 of the catheter body 104, the guidewire 300 is loaded into the catheter 100. In other words, the guidewire 300 extends through the entire length of the catheter body 104.

While methods have been described where the guidewire 300 is inserted into the first capture flare 124, and the guidewire 300 and first capture flare 124 are advanced through the internal lumen 106 of the catheter body 104 and exit the catheter body 104 through the second opening 110 of the catheter body (for instance by pulling on the second end 130 of the snare body 122), it should be appreciated that this is a non-limiting example. For example, in other embodiments, the guidewire 300 may be inserted into the second capture flare 128. The second capture flare 128, including the guidewire 300, may then be advanced into the internal lumen of the catheter body 104 through the second opening 110 of the catheter body 104. The second capture flare 128 and guidewire 300 may then be further advanced through the internal lumen of the catheter body 104 and exit the catheter body 104 through the first opening 108 of the catheter body 104 (for instance by pulling on the first end 126 of the snare body 122). As with the first capture flare 124, the second capture flare 128 may be biased to an open configuration as described above with respect to the first capture flare 124.

Embodiments can be described with reference to the following numerical clause:

1. A guidewire loading system, comprising: a catheter comprising a catheter body defining an internal lumen; and a snare at least partially positioned within the internal lumen of the catheter body, the snare comprising: a snare body; and a first capture flare extending from a first end of the snare body and configured to receive a guidewire, wherein the catheter body compresses the first capture flare to form a friction grip around the guidewire when the snare, including the first capture flare, and the guidewire are pulled at least partially through the internal lumen of the catheter body.

2. The guidewire loading system of clause 1, wherein: the snare further comprises a second capture flare extending from a second end of the snare body and configured to receive the guidewire, and the catheter body compresses the second capture flare to form a friction grip around the guidewire when the snare, including the second capture flare, and the guidewire are pulled at least partially through the internal lumen of the catheter body.

3. The guidewire loading system of any preceding clause, wherein the snare is pre-loaded within the internal lumen of the catheter body such that the snare is in a pre-loaded configuration prior to receiving the guidewire.

4. The guidewire loading system of clause 3, wherein when the snare is in the pre-loaded configuration, the first capture flare at least partially extends outside the internal lumen of the catheter body.

5. The guidewire loading system of any preceding clause, wherein the first capture flare comprises a wire mesh.

6. The guidewire loading system of any preceding clause, wherein the first capture flare comprises a polymeric film.

7. The guidewire loading system of any preceding clause, wherein the first capture flare comprises: a mesh; a first polymeric film layer on a first side of the mesh layer; and a second polymeric film layer on a second side of the mesh layer, opposite the first side.

8. A guidewire snare, comprising: a snare body; a first capture flare extending from a first end of the snare body and configured to receive a guidewire; and a second capture flare extending from a second end of the snare body and configured to receive the guidewire, wherein: the first capture flare is configured to form a friction fit around the guidewire when the first capture flare is pulled at least partially through an internal lumen of a catheter body; and the second capture flare is configured to form a friction fit around the guidewire when the second capture flare is pulled at least partially through the internal lumen of the catheter body.

9. The guidewire snare of clause 8, wherein the first capture flare is biasing to an open configuration.

10. The guidewire snare of any preceding clause, wherein the second capture flare is biased to a compressed configuration.

11. The guidewire snare of any preceding clause, wherein the first capture flare is funnel-shaped.

12. The guidewire snare of any preceding clause, wherein the second capture flare is funnel-shaped.

13. The guidewire snare of any preceding clause, wherein at least one of the first capture flare or the second capture flare comprises a wire mesh.

14. The guidewire snare of any preceding clause, wherein at least one of the first capture flare or the second capture flare comprises a polymeric film.

15. A method of loading a guidewire into a catheter, comprising: advancing the guidewire into a capture flare of a snare, the snare comprising: a snare body; and the capture flare extending from an end of the snare body and configured to receive the guidewire, wherein: the snare body is positioned at least partially within an internal lumen of a catheter body of the catheter; and the capture flare at least partially extends outside the internal lumen of the catheter body; and pulling the snare and the guidewire at least partially through the internal lumen of the catheter body such that the catheter body compresses the capture flare to form a friction grip around the guidewire.

16. The method of any preceding clause, wherein the snare is pre-loaded within the internal lumen of the catheter body.

17. The method of any preceding clause, wherein the capture flare comprises a wire mesh.

18. The method of any preceding clause, wherein the capture flare comprises a polymeric film.

19. The method of any preceding clause, wherein the first capture flare comprises: a mesh; a first polymeric film layer on a first side of the mesh layer; and a second polymeric film layer on a second side of the mesh layer, opposite the first side.

20. The method of any preceding clause, further comprising pulling the snare fully through the internal lumen of the catheter body.

It should now be understood that embodiments of the present disclosure are directed to devices, systems, and methods for loading a guidewire into a catheter. The embodiments particularly include guidewire snares having capture flares. The guidewire snare may come pre-loaded into a catheter. That is, catheter and snare may be assembled such that the snare is already contained within the catheter body when the device/system is delivered to a physician. The capture flare extends from an end of a snare body of the snare. An open end of the capture flare has a diameter greater than that of the catheter body, such that a physician may be able to insert the guidewire into the capture flare with a lesser degree of precision than needed to insert the guidewire directly into the catheter body. The guidewire and snare may then be advanced into the catheter body, which is sized to exhibit a compression force on the capture flare, causing the capture flare to collapse and form a friction grip around the guidewire. A second end of the snare may then be manipulated without the need to independently handle the guidewire, to advance the guidewire fully through the catheter body.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A guidewire loading system, comprising:

a catheter comprising an elongate catheter body defining an internal lumen, wherein the catheter is sized to traverse through a subject's vasculature; and a snare at least partially positioned within the internal lumen of the catheter body, the snare comprising:

a snare body; and a first capture flare extending from a first end of the snare body and a second capture flare extending from a second end of the snare body, wherein:

the first capture flare and the second capture flare have frustoconical outer surfaces in an uncompressed configuration;

the first capture flare is configured to receive a guidewire, wherein the catheter body compresses the first capture flare to form a friction grip around the guidewire when the snare, including the first capture flare, and the guidewire are pulled at least partially through the internal lumen of the catheter body; and the second capture flare is configured to receive the guidewire, wherein the catheter body compresses the second capture flare to form a friction grip around the guidewire when the snare, including the second capture flare, and the guidewire are pulled at least partially through the internal lumen of the catheter body.

2. The guidewire loading system of claim 1, wherein the snare is pre-loaded within the internal lumen of the catheter body such that the snare is in a pre-loaded configuration prior to receiving the guidewire.

3. The guidewire loading system of claim 2, wherein when the snare is in the pre-loaded configuration, the first capture flare at least partially extends outside the internal lumen of the catheter body.

4. The guidewire loading system of claim 1, wherein the first capture flare comprises a wire mesh.

5. The guidewire loading system of claim 1, wherein the first capture flare comprises a polymeric film.

6. The guidewire loading system of claim 1, wherein the first capture flare comprises:

a mesh;

a first polymeric film layer on a first side of the mesh; and a second polymeric film layer on a second side of the mesh, opposite the first side.

7. A guidewire snare, comprising:

a snare body;

a first capture flare extending from a first end of the snare body and configured to receive a guidewire; and a second capture flare extending from a second end of the snare body and configured to receive the guidewire, wherein:

the first capture flare and the second capture flare have frustoconical outer surfaces in an uncompressed configuration;

the first capture flare is configured to form a friction fit around the guidewire when the first capture flare is pulled at least partially through an internal lumen of a catheter body; and the second capture flare is configured to form a friction fit around the guidewire when the second capture flare is pulled at least partially through the internal lumen of the catheter body.

8. The guidewire snare of claim 7, wherein the first capture flare is biased to an open configuration.

9. The guidewire snare of claim 8, wherein the second capture flare is biased to a compressed configuration.

10. The guidewire snare of claim 8, wherein the first capture flare is funnel-shaped.

11. The guidewire snare of claim 8, wherein the second capture flare is funnel-shaped.

12. The guidewire snare of claim 7, wherein at least one of the first capture flare or the second capture flare comprises a wire mesh.

13. The guidewire snare of claim 7, wherein at least one of the first capture flare or the second capture flare comprises a polymeric film.

* * * * *